US012588840B2

(12) United States Patent
Tsai et al.

(10) Patent No.: US 12,588,840 B2
(45) Date of Patent: Mar. 31, 2026

(54) BLOOD OXYGEN CONCENTRATION MEASUREMENT DEVICE AND METHOD

(71) Applicant: Quanta Computer Inc., Taoyuan City (TW)

(72) Inventors: Peng-Zhe Tsai, Taoyuan City (TW); Yung-Ming Chung, Taoyuan City (TW)

(73) Assignee: QUANTA COMPUTER INC., Taoyuan City (TW)

( * ) Notice: Subject to any disclaimer, the term of this patent is extended or adjusted under 35 U.S.C. 154(b) by 412 days.

(21) Appl. No.: 18/302,204

(22) Filed: Apr. 18, 2023

(65) Prior Publication Data

US 2024/0225494 A1     Jul. 11, 2024

(30) Foreign Application Priority Data

Jan. 11, 2023     (TW) ................................. 112101142

(51) Int. Cl.
*A61B 5/1455*          (2006.01)

(52) U.S. Cl.
CPC ................................ *A61B 5/14551* (2013.01)

(58) Field of Classification Search
CPC ............ A61B 5/14551; A61B 5/14552; A61B 5/0205; A61B 5/7225; A61B 5/725
See application file for complete search history.

(56) References Cited

U.S. PATENT DOCUMENTS

| | | | | |
|---|---|---|---|---|
| 2008/0103375 A1* | 5/2008 | Kiani | ................... | A61B 5/0002 |
| | | | | 600/323 |
| 2009/0030330 A1* | 1/2009 | Kiani | ................... | A61B 5/0261 |
| | | | | 600/500 |

(Continued)

FOREIGN PATENT DOCUMENTS

| | | |
|---|---|---|
| CN | 112494025 A | 3/2021 |
| CN | 112638242 A | 4/2021 |

(Continued)

OTHER PUBLICATIONS

Chinese language office action dated May 17, 2023, issued in application No. TW 112101142.

(Continued)

*Primary Examiner* — Abid A Mustansir
(74) *Attorney, Agent, or Firm* — McClure, Qualey & Rodack, LLP

(57) ABSTRACT

A blood oxygen concentration measurement device includes a light source unit, a light detection unit, a signal processing circuit, and a control unit. The light source generates a light signal. The light detection unit receives a penetrating signal generated by the light signal penetrating an object to generate a detection signal. The signal processing circuit receives the detection signal and processes the detection signal to generate a first processing signal. The control unit receives the first processing signal, calculates the blood oxygen value, the pulse rate and the signal strength index according to the first processing signal, and outputs the blood oxygen value, the pulse rate, and the signal strength index, or performs a low perfusion signal measurement process according to the signal strength index and the first predetermined index.

12 Claims, 8 Drawing Sheets

(56)        References Cited

U.S. PATENT DOCUMENTS

| 2010/0121164 A1* | 5/2010 | Donars ............. | A61B 5/14551 |
| | | | 600/323 |
| 2020/0060555 A1 | 2/2020 | Lamego | |
| 2022/0233112 A1 | 7/2022 | Liu et al. | |

FOREIGN PATENT DOCUMENTS

| CN | 113440118 A | 9/2021 |
| TW | 202228594 A | 8/2022 |

OTHER PUBLICATIONS

Chinese language office action dated Jul. 22, 2024, issued in application No. TW 112101142.

* cited by examiner the control unit generating a first parameter setting or a second parameter setting to the signal processing circuit according to the signal strength index and a second predetermined index — S402

FIG. 4 the signal processing circuit
converting the detection signal
according to the reduced
current-to-voltage gain to generate a
voltage signal ⎯ S602 multiplying the voltage signal by the
maintained linear gain to generate a
gain signal ⎯ S604 filtering the gain signal according to
the expanded filter bandwidth to
generate the first processing signal ⎯ S606

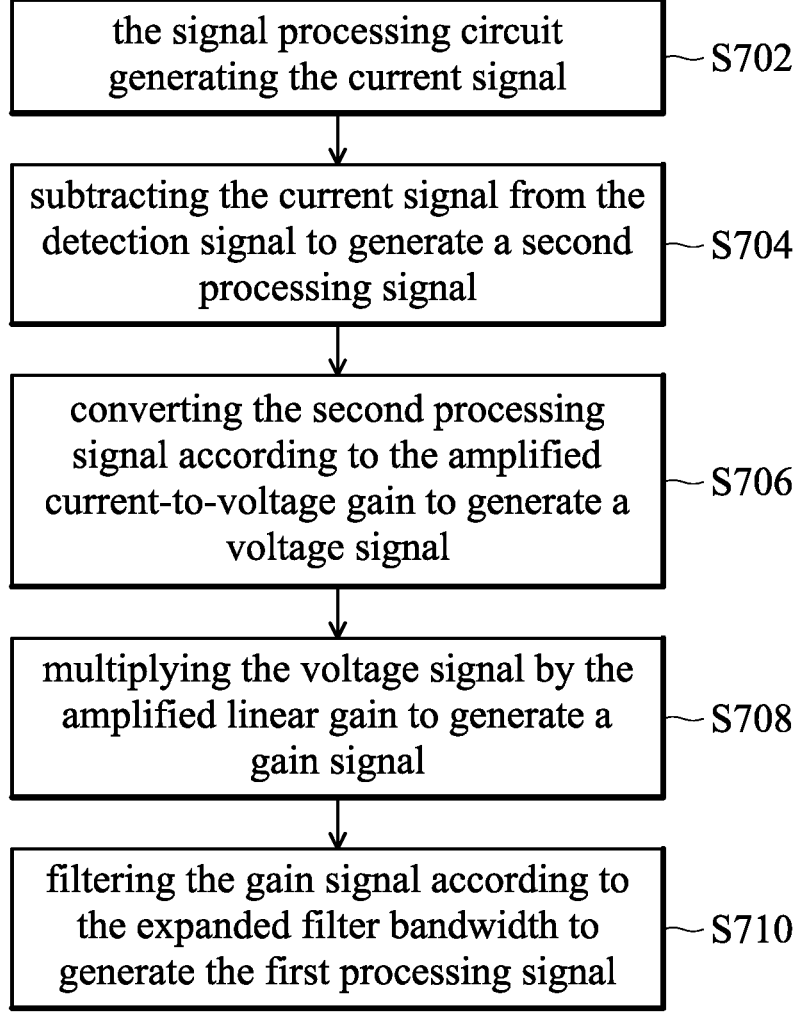

the signal processing circuit generating the current signal        ⏤S702 subtracting the current signal from the detection signal to generate a second processing signal        ⏤S704 converting the second processing signal according to the amplified current-to-voltage gain to generate a voltage signal        ⏤S706 multiplying the voltage signal by the amplified linear gain to generate a gain signal        ⏤S708 filtering the gain signal according to the expanded filter bandwidth to generate the first processing signal        ⏤S710

FIG. 7

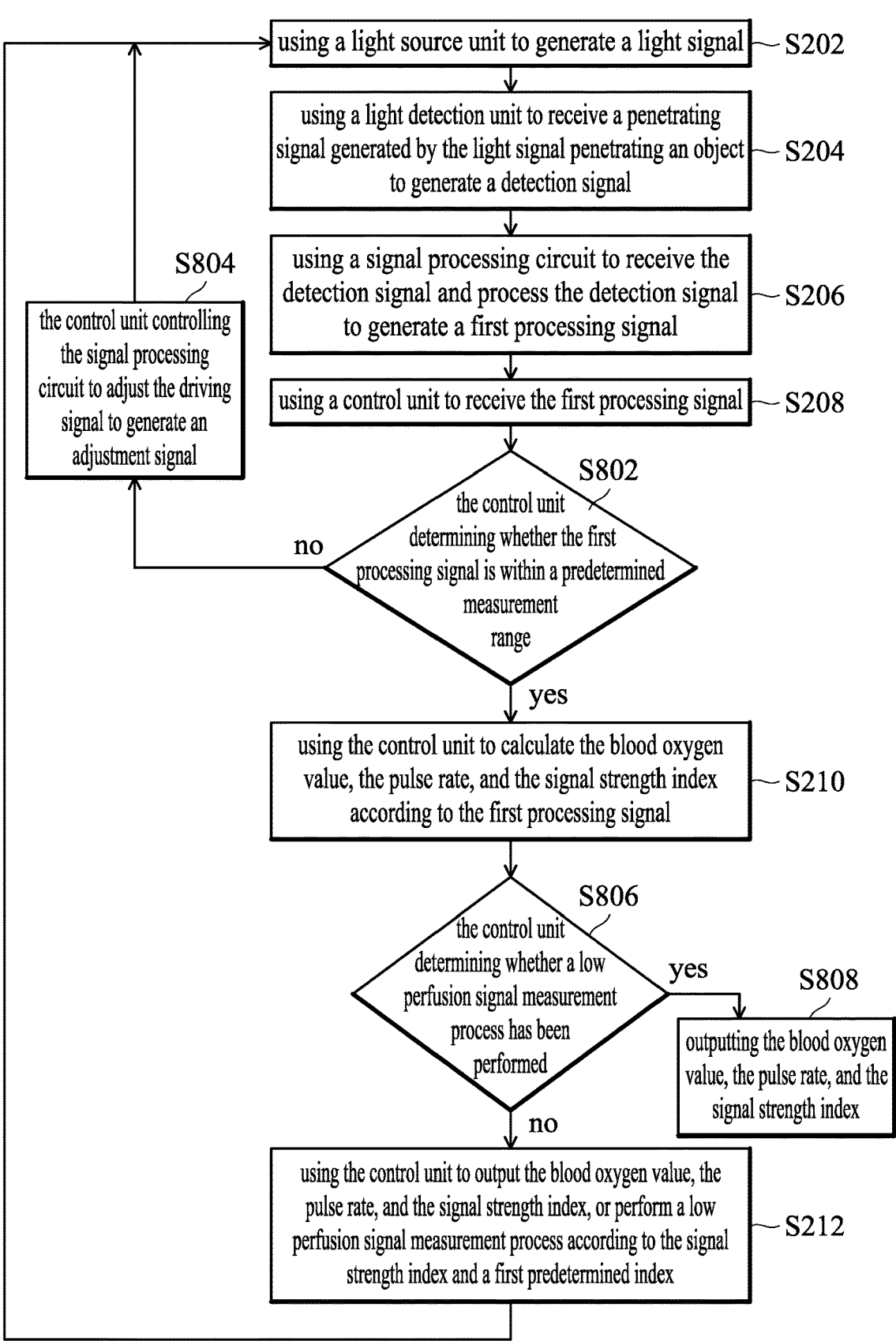

using a light source unit to generate a light signal — S202 using a light detection unit to receive a penetrating signal generated by the light signal penetrating an object to generate a detection signal — S204 using a signal processing circuit to receive the detection signal and process the detection signal to generate a first processing signal — S206 using a control unit to receive the first processing signal — S208

S802 the control unit determining whether the first processing signal is within a predetermined measurement range no S804 the control unit controlling the signal processing circuit to adjust the driving signal to generate an adjustment signal yes using the control unit to calculate the blood oxygen value, the pulse rate, and the signal strength index according to the first processing signal — S210

S806 the control unit determining whether a low perfusion signal measurement process has been performed yes S808 outputting the blood oxygen value, the pulse rate, and the signal strength index no using the control unit to output the blood oxygen value, the pulse rate, and the signal strength index, or perform a low perfusion signal measurement process according to the signal strength index and a first predetermined index — S212

FIG. 8

BLOOD OXYGEN CONCENTRATION MEASUREMENT DEVICE AND METHOD

CROSS REFERENCE TO RELATED APPLICATIONS

This application claims priority of Taiwan Patent Application No. 112101142, filed on Jan. 11, 2023, the entirety of which is incorporated by reference herein.

BACKGROUND OF THE INVENTION

Field of the Invention

The present invention relates to a measurement device and method, and in particular it relates to a blood oxygen concentration measurement device and method.

Description of the Related Art

In general, the measurement of blood oxygen concentration is mainly used to determine the oxygen content in the blood of a patient, as this is an important vital indictor that may be used as a reference for treatment. However, due to the influence of diseases or changes in the external environment, the human body can self-regulate to reduce the supply of blood and nutrients to remote peripheral tissues, thereby reducing the amount of blood circulation to the peripheral microvessels, resulting in the signal used to measure blood oxygen (such as the photoplethysmography (PPG) signal) becoming very weak. In addition, according the definition used by clinicians, academics, and the US FDA, when the signal intensity of the aforementioned signal is ≤0.3%, this phenomenon is called low perfusion, and it may make it difficult for a general oximeter to measure accurately, resulting in an incorrect diagnosis. Therefore, how to effectively increase the accuracy of measuring blood oxygen concentration has become a focus for technical improvements by various manufacturers.

BRIEF SUMMARY OF THE INVENTION

An embodiment of the present invention provides a blood oxygen concentration measurement device and method, thereby increasing the accuracy of the blood oxygen concentration measurements, and increasing the convenience of use.

An embodiment of the present invention provides a blood oxygen concentration measurement device, which includes a light source unit, a light detection unit, a signal processing circuit, and a control unit. The light source unit is configured to generate a light signal. The light detection unit is configured to receive a penetrating signal generated by the light signal penetrating an object to generate a detection signal. The signal processing circuit is configured to receive the detection signal and process the detection signal to generate a first processing signal. The control unit is configured to receive the first processing signal, calculate the blood oxygen value, the pulse rate, and the signal strength index according to the first processing signal, and output the blood oxygen value, the pulse rate, and the signal strength index or perform a low perfusion signal measurement process according to the signal strength index and the first predetermined index.

An embodiment of the present invention provides a blood oxygen concentration measurement method, which includes the following steps. A light source unit is used to generate a light signal. A light detection unit is used to receive a penetrating signal generated by the light signal penetrating an object to generate a detection signal. A signal processing circuit is used to receive the detection signal and process the detection signal to generate a first processing signal. The control unit is used to receive the first processing signal, calculate the blood oxygen value, the pulse rate, and the signal strength index according to the first processing signal, and output the blood oxygen value, the pulse rate, and the signal strength index, or perform a low perfusion signal measurement process according to the signal strength index and the first predetermined index.

According to the blood oxygen concentration measurement device and method disclosed by the present invention, the light detection unit receives the penetrating signal generated by the light signal penetrating the object to generate the detection signal. The signal processing circuit processes the detection signal to generate the first processing signal. The control unit calculates the blood oxygen value, the pulse rate, and the signal strength index according to the first processing signal. The control unit outputs the blood oxygen value, the pulse rate, and the signal strength index, or performs the low perfusion signal measurement process according to the signal strength index and the first predetermined index. Therefore, the accuracy of the blood oxygen concentration measurement may be effectively increased, and the convenience of use is increased.

BRIEF DESCRIPTION OF THE DRAWINGS

The present invention can be more fully understood by reading the subsequent detailed description and examples with references made to the accompanying drawings, wherein:

FIG. 4 is a detailed flowchart of step S306 in FIG. 3;

FIG. 7 is another detailed flowchart of step S206 in FIG. 2; and

FIG. 8 is a flowchart of a blood oxygen concentration measurement method according another embodiment of the present invention.

DETAILED DESCRIPTION OF THE INVENTION

In each of the following embodiments, the same reference number represents an element or component that is the same or similar.

Figure 1:
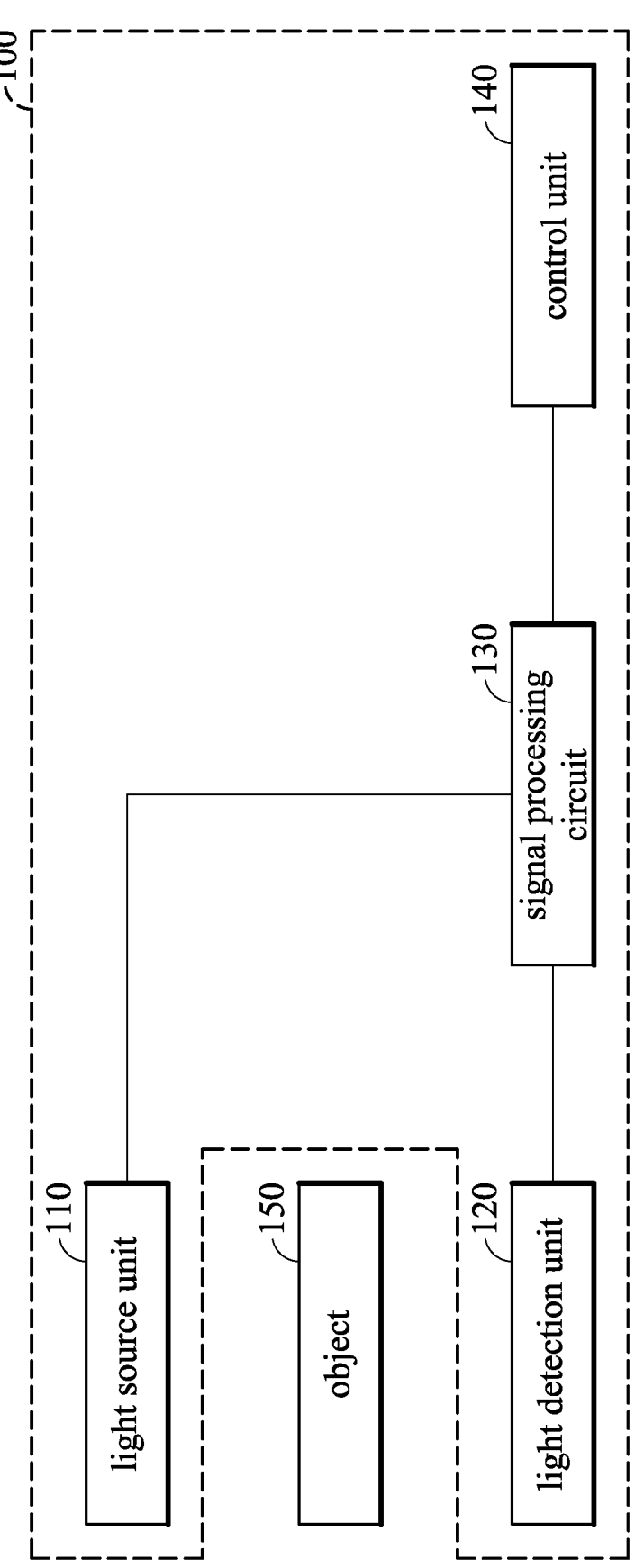
FIG. 1 is a schematic view of a blood oxygen concentration measurement device according an embodiment of the present invention.

FIG. 1 is a schematic view of a blood oxygen concentration measurement device according an embodiment of the present invention. Please refer to FIG. 1. The blood oxygen concentration measurement device 100 includes a light source unit 110, a light detection unit 120, a signal processing circuit 130 and a control unit 140.

The light source unit 110 may generate a light signal. In the embodiment, the light source unit 110 may include a red light-emitting diode and an infrared light-emitting diode, and the light signal may include a red light signal and an infrared light signal, but the embodiment of the present invention is not limited thereto.

The light detection unit 120 may receive a penetrating signal generated by the light signal penetrating an object 150 to generate a detection signal. That is, the light detection unit 120 may be disposed opposite to the light source unit 110, and the object 150 may be placed between the light source unit 110 and the light detection unit 120. Accordingly, the light source unit 110 may generate the light signal to the object 150, the light signal may penetrates the object 150 to generate the penetrating signal, the penetrating signal may be transmitted to the light detection unit 120, and the light detection unit 120 receives the penetrating signal to generate the corresponding detection signal. In the embodiment, the above object 150 is, for example, a finger of a user, but the embodiment of the present invention is not limited thereto. In addition, the light detection unit 120 may be a photodiode or another suitable photodetector, and the detection signal may be a current signal of a photoplethysmogram (PPG) signal, but the embodiment of the present invention is not limited thereto.

The signal processing circuit 130 may be coupled to the light detection unit 120 and the light source unit 110. The signal processing circuit 130 may provide a driving signal to the light source unit 110, so that the light source unit 110 may generate the light signal to the object 150. The signal processing circuit 130 may receive the detection signal generated by the light detection unit 120, and process the detection signal to generate a first processing signal. Furthermore, the signal processing circuit 130 may process the detection signal according to an original parameter setting, so as to generate the first processing signal. In the embodiment, the original parameter setting may at least include a current-to-voltage gain, a linear gain and a filter bandwidth. In addition, the current-to-voltage gain is, for example, 250K, the linear gain is, for example, 3 times, and the filter bandwidth is, for example, 0.4~10 Hz, but the embodiment of the present invention is not limited thereto.

For example, the signal processing circuit 130 may convert the detection signal according to the current-to-voltage gain of 250K to generate a voltage signal. Then, the signal processing circuit 130 may multiply the voltage signal by the linear gain of 3 times to generate a gain signal. Afterward, the signal processing circuit 130 may filter the gain signal according to the filter bandwidth of 0.4~10 Hz to generate the first processing signal. In the embodiment, the signal processing circuit 130 may be a printed circuit board (PCB) or an integrated circuit (IC) including a processing circuit, but the embodiment of the present invention is not limited thereto. In addition, the first processing signal may include a red direct current (DC) signal, a red alternating current (AC) signal, an infrared direct current signal and an infrared alternating current signal.

The control unit 140 may be coupled to the signal processing circuit 130. The control unit 140 may receive the first processing signal. Afterward, the control unit 140 may calculate the blood oxygen value (blood oxygen saturation (SpO2)), the pulse rate (PR), and the signal strength index according to the first processing signal. In the embodiment, the blood oxygen value may be calculated according to the red direct current signal, the red alternating current signal, the infrared direct current signal and the infrared alternating current signal of the first processing signal. For example, the blood oxygen value=(the red alternating current signal/the red direct current signal)/(the infrared alternating current signal/the infrared direct current signal). The pulse rate is calculated according to the red alternating current signal or the infrared alternating current signal, for example, the pulse rate is calculated according to the peak and trough (i.e., peak-to-peak value) of the red alternating current signal or the infrared alternating current signal. The signal strength index is calculated according to the infrared direct current signal and the infrared alternating current signal of the first processing signal, for example, the signal strength index= (the infrared alternating current signal/the infrared direct current signal). In addition, the signal strength index may be a perfusion index (PI). Furthermore, in the embodiment, the control unit 140 may be a micro control unit (MCU) or another suitable controller, but the embodiment of the present invention is not limited thereto.

In addition, in some embodiment, before the control unit 140 calculates the blood oxygen value, the pulse rate, and the signal strength index according to the first processing signal, the control unit 140 may determine whether the first processing is within a predetermined measurement range. In the embodiment, the original parameter setting may also include the predetermined measurement range, and the pre- determined measurement range may include a direct current upper limit value and a direct current lower limit value, wherein the direct current upper limit value is, for example, 1.026V, and the direct current lower limit value is, for example, 0.028V (i.e., the predetermined measurement range is 0.028V~1.026V), but the embodiment of the present invention is not limited thereto. That is, the control unit 140 may determine whether the red direct current signal or the infrared direct current signal of the first processing signal is within the predetermined measurement range.

When the control unit 140 determines that the first pro- cessing signal is not within the predetermined measurement range, the control unit 140 may control the signal processing circuit 140 to adjust the driving signal to generate the adjustment signal, so that the light source unit 110 may generate the corresponding light signal according to the adjustment signal, and the first processing signal may be within the predetermined measurement range. When the control unit 140 determines that the first processing signal is within the predetermined measurement range, the control unit 140 may receive the first processing signal, calculate the blood oxygen value, the pulse rate, and the signal strength index according to the first processing signal, and output the blood oxygen value, the pulse rate, and the signal strength index, or perform the low perfusion signal measurement process according to the signal strength index and the first predetermined index.

Then, the control unit 140 may output the blood oxygen value, the pulse rate, and the signal strength index, or perform the low perfusion signal measurement process according to the signal strength index and the first prede- termined index. In the embodiment, the first predetermined index is 0.8, for example, but the embodiment of the present invention is not limited thereto.

Furthermore, the control unit 140 may compare the signal strength index with the first predetermined index (such as 0.8), so as to determine whether the signal strength index is greater than the first predetermined index (such as 0.8). When the control unit 140 determines that the signal strength index is greater than the first predetermined index (such as 0.8), this indicates that the signal strength index is not in a low perfusion state (i.e., the signal strength index>0.8), the control unit 140 may output the blood oxygen value, the pulse rate, and the signal strength index. For example, the control unit 140 may output the blood oxygen value, the pulse rate, and the signal strength index to a display unit (not shown), so that the display unit displays the blood oxygen value, the pulse rate, and the signal strength index. When the control unit 140 determines that the signal strength index is not greater than the first predetermined index (such as 0.8), the control unit 140 may perform a low perfusion signal measurement process.

In some embodiments, when the control unit 140 performs a low perfusion signal measurement process, the control unit 140 may generate a first parameter setting or a second parameter setting to the signal processing circuit 130 according to the signal strength index and a second predetermined index. In the embodiment, the second predetermined index is, for example, less than the first predetermined index, and the second predetermined index is, for example, 0.1, but the embodiment of the present invention is not limited thereto. Furthermore, the control unit 140 may compare the signal strength index with the second predetermined index (such as 0.1), so as to determine whether the signal strength index is less than the second predetermined index (such as 0.1).

When the control unit 140 determines that the signal strength index is not less than the second predetermined index (such as 0.1), this indicates that the signal strength index is between 0.8 and 0.1 (such as 0.1<the signal strength index<0.8), and the control unit 140 may generate the first parameter setting to the signal processing circuit 130. In addition, when the control unit 140 determines that the signal strength index is less than the second predetermined index (such as 0.1), this indicates that the signal strength index<0.1, and the control unit 140 may generate the second parameter setting to the signal processing circuit 130.

Then, the signal processing circuit 130 may process according to the first parameter setting or the second parameter setting to generate the first processing signal. In some embodiments, the above first parameter setting may at least include an adjusted predetermined measurement range, a reduced current-to-voltage gain, a maintained linear gain, and an expanded filter bandwidth. In the embodiment, the adjusted predetermined measurement range is, for example, 0.8008V~1.026V (i.e., the direct current upper limit value of the adjusted predetermined measurement range is equal to the direct current upper limit value of 1.026V of the original parameter setting, and the direct current lower limit value of the adjusted predetermined measurement range is greater than the direct current lower limit value of 0.228V of the original parameter setting). The reduced current-to-voltage gain is, for example, 100K (i.e., the reduced current-to-voltage gain is less than the current-to-voltage gain of 250K of the original parameter setting). The maintained linear gain is, for example, 3 times (i.e., the maintained linear gain is equal to the linear gain of 3 times of the original parameter setting). The expanded filter bandwidth is, for example, 0.1~15 Hz (i.e., the expanded filter bandwidth is wider than the filter bandwidth of 0.4~10 Hz of original parameter setting).

The control unit 140 may determine whether the first processing signal is within the adjusted predetermined measurement range according to the adjusted predetermined measurement range (such as 0.8008V~1.026V). In addition, the signal processing circuit 130 may convert the detection signal according to the reduced current-to-voltage gain (such as 100K) to generate the voltage signal. Then, the signal processing circuit 130 may multiply the above voltage signal by the maintained linear gain (such as 3 times) to generate the gain signal. Afterward, the signal processing circuit 130 may filter the above gain signal according to the expanded filter bandwidth (such as 0.1~15 Hz) to generate the first processing signal. Therefore, it may effectively improve the signal-to-noise ratio (SNR) of the signal and obtain more signal information (such as the signal waveform and quantity of the first processing signal), so as to increase the accuracy of blood oxygen concentration measurement and increase the convenience of use.

In some embodiments, the second parameter setting may at least include an adjusted predetermined measurement range, a current signal, an amplified current-to-voltage gain, an amplified linear gain and an expanded filter bandwidth. In the embodiment, the adjusted predetermined measurement range is, for example, 0.8008V~1.026V (i.e., the direct current upper limit value of the adjusted predetermined measurement range is equal to the direct current upper limit value of 1.026V of the original parameter setting, and the direct current lower limit value of the adjusted predetermined measurement range is greater than the direct current lower limit value of 0.228V of the original parameter setting). The current signal is, for example, 6 uA. The amplified current-to-voltage gain is, for example, 1M (i.e., the amplified current-to-voltage gain is greater than the current-to-voltage gain of 250K of the original parameter setting). The amplified linear gain is, for example, 4 times (i.e., the amplified linear gain is greater than the linear gain of 3 times of the original parameter setting). The expanded filter bandwidth is, for example, 0.1~15 Hz (i.e., the expanded filter bandwidth is wider than the filter bandwidth of 0.4~10 Hz of original parameter setting).

The control unit 140 may determine whether the first processing signal is within the adjusted predetermined measurement range according to the adjusted predetermined measurement range (such as 0.8008V~1.026V). In addition, the signal processing circuit 130 may generate the current signal (such as 6 uA). Then, the signal processing circuit 130 may subtract the above current signal (such as 6 uA) from the detection signal to generate a second processing signal, i.e., obtaining the processing signal with a low direct current level. Afterward, the signal processing circuit 130 may convert the above second processing signal according to the amplified current-to-voltage gain (such as 1M) to generate the voltage signal. Then, the signal processing circuit 130 may multiply the above voltage signal by the amplified linear gain (such as 4 times) to generate the gain signal. Afterward, the signal processing circuit 130 may filter the above gain signal according to the expanded filter bandwidth (such as 0.1~15 Hz) to generate the first processing signal. Therefore, it may effectively improve the signal-to-noise ratio of the signal and obtain more signal information (such as the signal waveform and quantity of the first processing signal), so as to increase the accuracy of blood oxygen concentration measurement and increase the convenience of use.

In some embodiments, after the control unit 140 calculates the blood oxygen value, the pulse rate, and the signal strength index according to the first processing signal, the control unit 140 may determine whether the low perfusion signal measurement process has been performed. When the control unit 140 determines that the low perfusion signal measurement process has not been performed, the control unit 140 may output the blood oxygen value, the pulse rate, and the signal strength index, or perform the low perfusion signal measurement process according to the signal strength index and the first predetermined index, so as to perform subsequent operations. When the control unit 140 determines that a low perfusion signal measurement process has been performed, the control unit 140 may directly output the blood oxygen value, the pulse rate, and the signal strength index.

Figure 2:
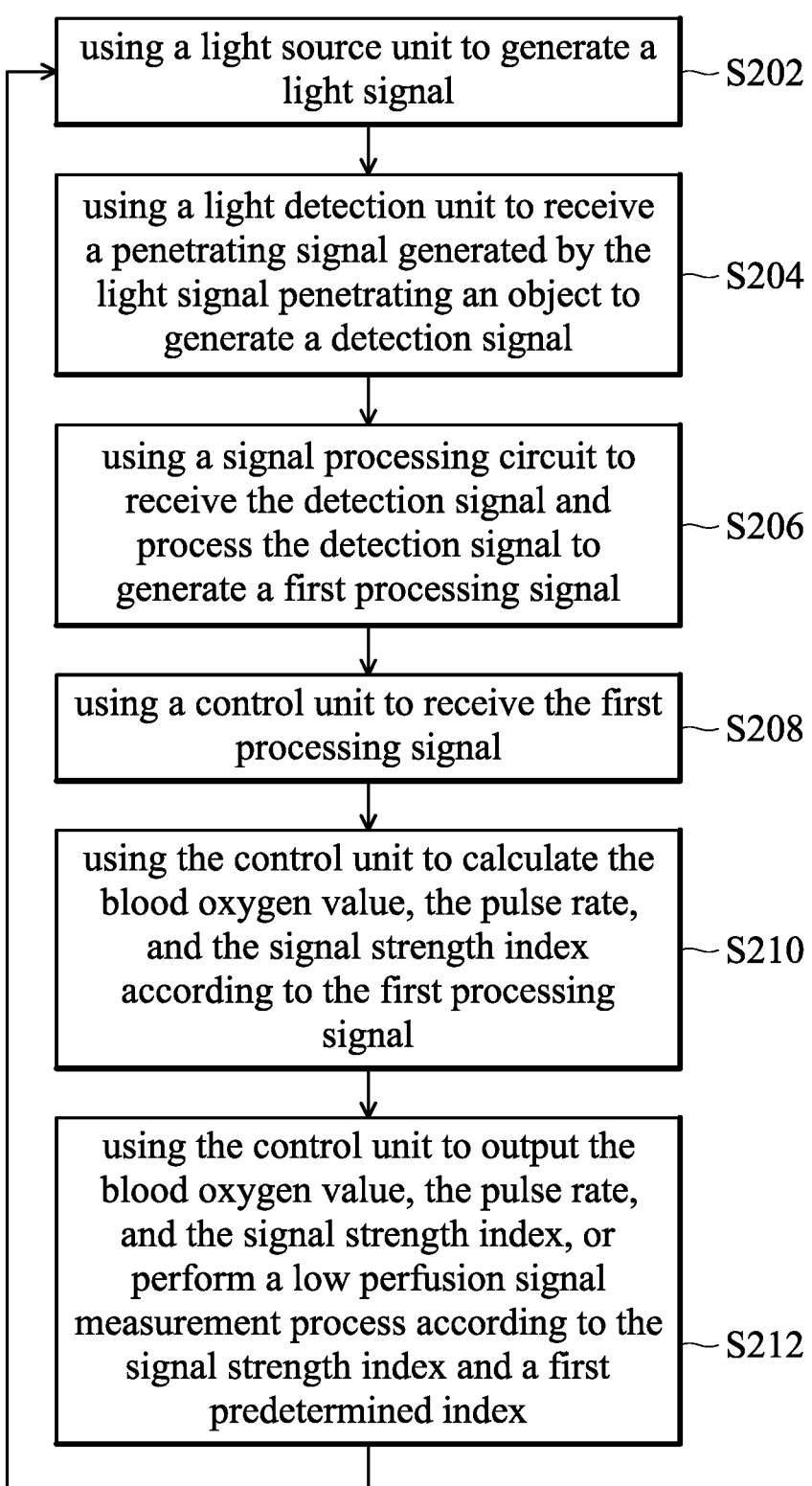
FIG. 2 is a flowchart of a blood oxygen concentration measurement method according an embodiment of the present invention.

FIG. 2 is a flowchart of a blood oxygen concentration measurement method according an embodiment of the present invention. In step S202, the method involves using a light source unit to generate a light signal. In step S204, the method involves using a light detection unit to receive a penetrating signal generated by the light signal penetrating an object to generate a detection signal. In step S206, the method involves using a signal processing circuit to receive the detection signal and process the detection signal to generate a first processing signal.

In step S208, the method involves using a control unit to receive the first processing signal. In step S210, the method involves using the control unit to calculate the blood oxygen value, the pulse rate, and the signal strength index according to the first processing signal. In step S212, the method involves using the control unit to output the blood oxygen value, the pulse rate, and the signal strength index, or perform a low perfusion signal measurement process according to the signal strength index and a first predetermined index. In the embodiment, the above light signal includes, for example, a red light signal and an infrared light signal.

Figure 3:
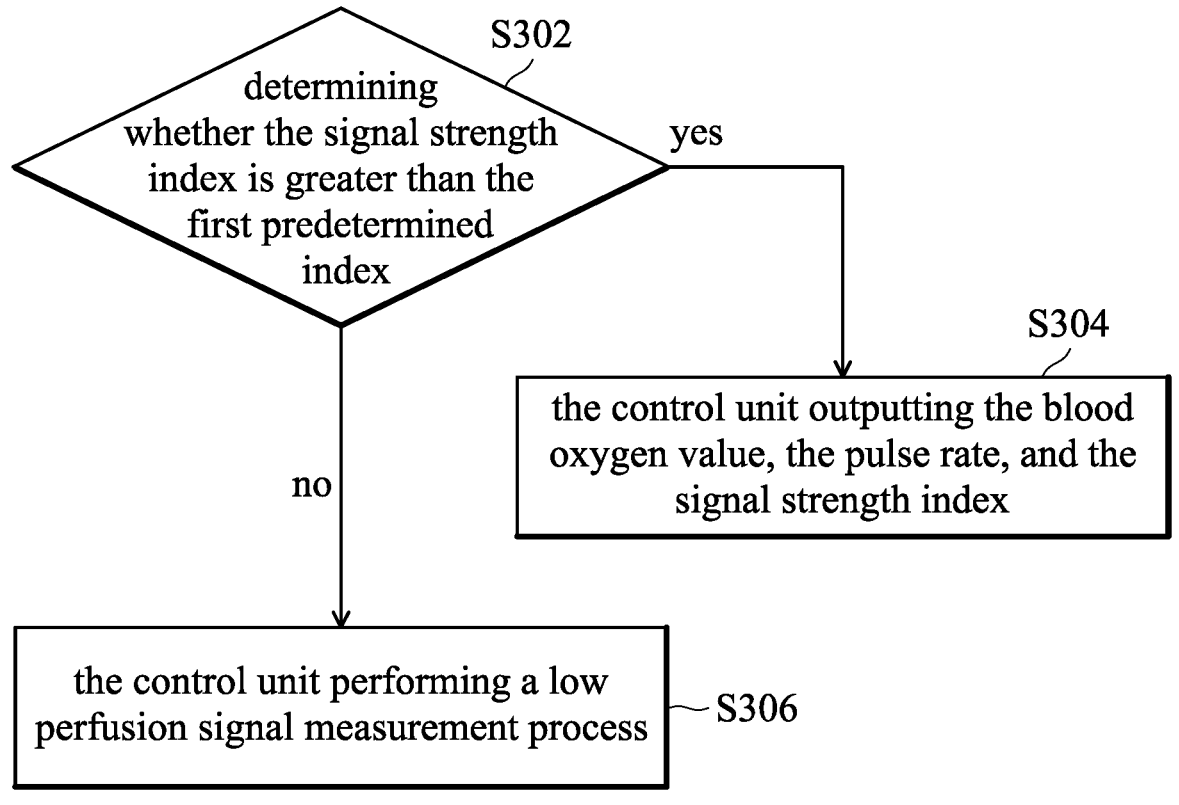
FIG. 3 is a detailed flowchart of step S212 in FIG. 2.

FIG. 3 is a detailed flowchart of step S212 in FIG. 2. In step S302, the method involves determining whether the signal strength index is greater than the first predetermined index. When the control unit determines that the signal strength index is greater than the first predetermined index, the method performs step S304. In step S304, the method involves the control unit outputting the blood oxygen value, the pulse rate, and the signal strength index. When the control unit determines that the signal strength index is not greater than the first predetermined index, the method performs step S306. In step S306, the method involves the control unit performing a low perfusion signal measurement process.

Figure 4:
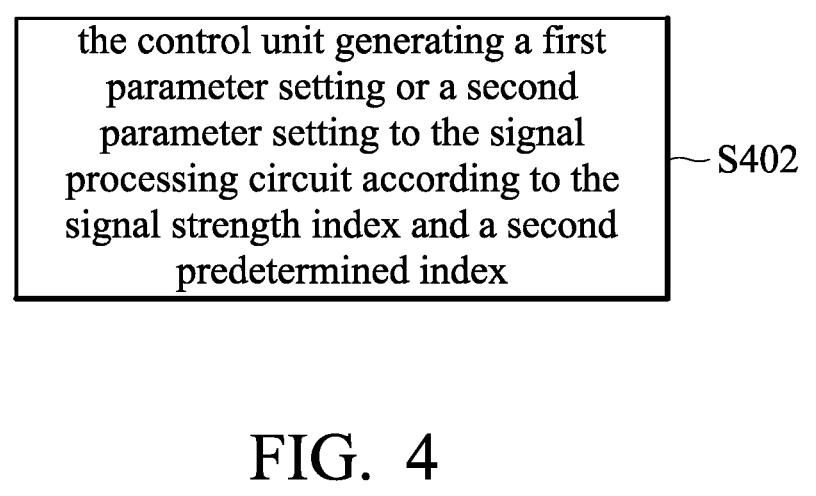

FIG. 4 is a detailed flowchart of step S306 in FIG. 3. In step S402, the method involves the control unit generating a first parameter setting or a second parameter setting to the signal processing circuit according to the signal strength index and a second predetermined index, so that in step S206, the signal processing circuit may process the detection signal according to the first parameter setting or the second parameter setting, so as to generate the first processing signal. In the embodiment, the second predetermined index is, for example, less than the first predetermined index.

Figure 5:
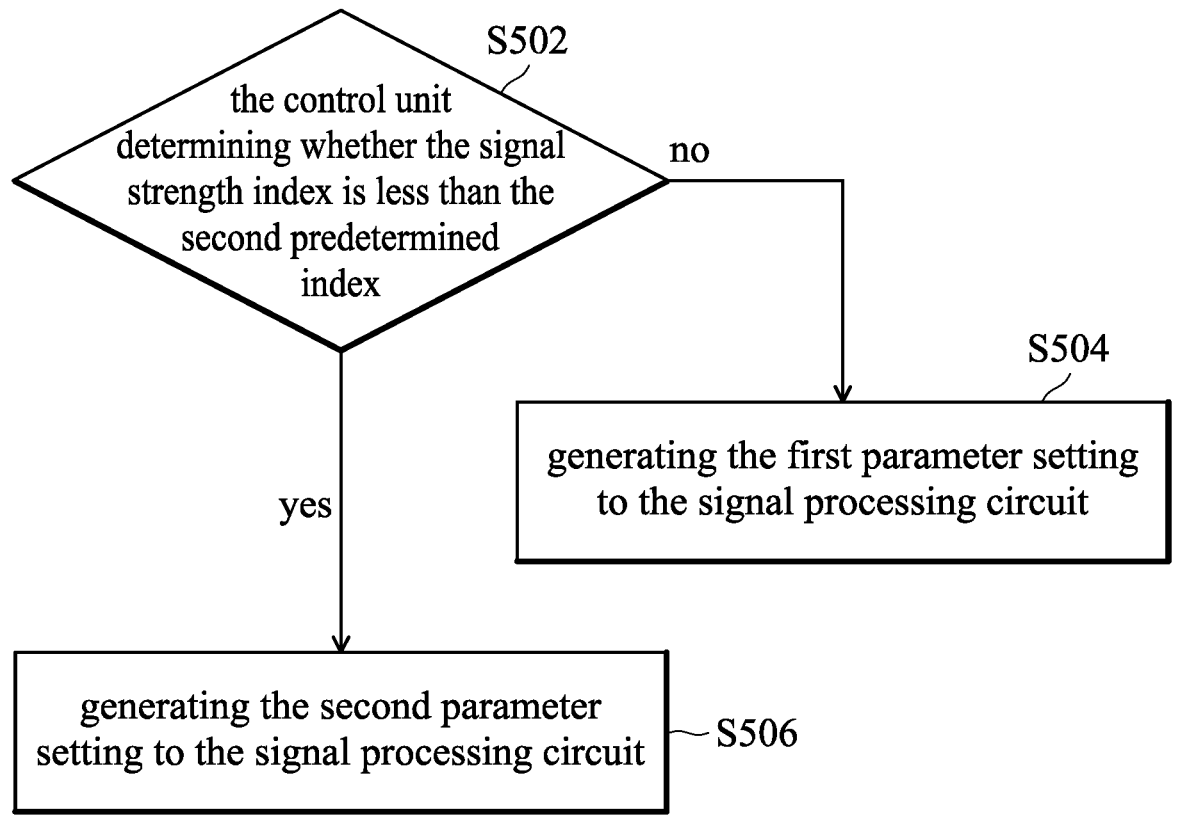
FIG. 5 is a detailed flowchart of step S402 in FIG. 4.

FIG. 5 is a detailed flowchart of step S402 in FIG. 4. In step S502, the method involves the control unit determining whether the signal strength index is less than the second predetermined index. When the control unit determines that the signal strength index is not less than the second predetermined index, the method performs step S504. In step S504, the method involves generating the first parameter setting to the signal processing circuit. When the control unit determines that the signal strength index is less than the second predetermined index, the method performs step S506. In step S506, the method involves generating the second parameter setting to the signal processing circuit.

Figure 6:
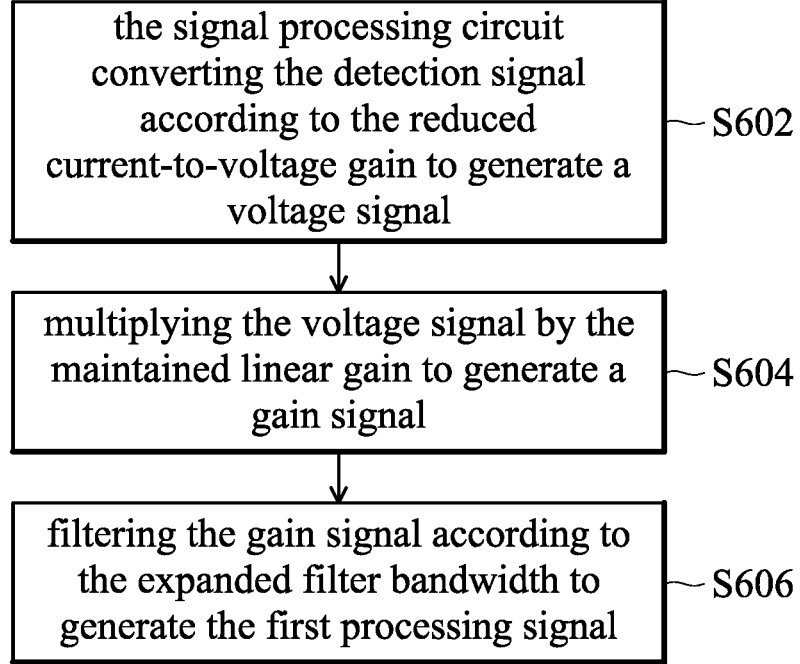
FIG. 6 is a detailed flowchart of step S206 in FIG. 2.

FIG. 6 is a detailed flowchart of step S206 in FIG. 2. In the embodiment, the first parameter setting includes an adjusted predetermined measurement range, a reduced current-to-voltage gain, a maintained linear gain, and an expanded filter bandwidth. In step S602, the method involves the signal processing circuit converting the detection signal according to the reduced current-to-voltage gain to generate a voltage signal. In step S604, the method involves multiplying the voltage signal by the maintained linear gain to generate a gain signal. In step S606, the method involves filtering the gain signal according to the expanded filter bandwidth to generate the first processing signal.

FIG. 7 is another detailed flowchart of step S206 in FIG. 2. In the embodiment, the second parameter setting may include an adjusted predetermined measurement range, a current signal, an amplified current-to-voltage gain, an amplified linear gain and an expanded filter bandwidth. In step S702, the method involves the signal processing circuit generating the current signal. In step S704, the method involves subtracting the current signal from the detection signal to generate a second processing signal. In step S706, the method involves converting the second processing signal according to the amplified current-to-voltage gain to generate a voltage signal. In step S708, the method involves multiplying the voltage signal by the amplified linear gain to generate a gain signal. In step S710, the method involves filtering the gain signal according to the expanded filter bandwidth to generate the first processing signal.

FIG. 8 is a flowchart of a blood oxygen concentration measurement method according another embodiment of the present invention. In the embodiment, steps S202~S212 in FIG. 8 are the same as or similar to steps S202~S212 in FIG. 2. Accordingly, steps S202~S212 in FIG. 8 may refer to the description of the embodiment of FIG. 2, and the description thereof is not repeated herein. In step S802, the method involves the control unit determining whether the first processing signal is within a predetermined measurement range. When the control unit determines that the first processing signal is not within the predetermined measurement range, the method performs to step S804. In step S804, the method involves the control unit controlling the signal processing circuit to adjust the driving signal to generate an adjustment signal, and performs step S202, so that the light source unit may generate the light signal according to the adjustment signal. When the control unit determines that the first processing signal is within the predetermined measurement range, the method performs step S210 of using the control unit to calculate the blood oxygen value, the pulse rate, and the signal strength index according to the first processing signal.

In step S806, the method involves the control unit determining whether a low perfusion signal measurement process has been performed. When the control unit determines that a low perfusion signal measurement process has not been performed, the method performs step S212, so as to perform subsequent operations. When the control unit determines that a low perfusion signal measurement process has been performed, the method performs step S808. In step S808, the method involves outputting the blood oxygen value, the pulse rate, and the signal strength index.

In addition, in some embodiments, after performing the low perfusion signal measurement process, in step S802, the control unit may determine whether the first processing signal is within the adjusted predetermined measurement range according to the adjusted predetermined measurement range in the first parameter setting or the second parameter setting.

In summary, according to the blood oxygen concentration measurement device and method disclosed by the embodiment of the present invention, the light detection unit receives the penetrating signal generated by the light signal penetrating the object to generate the detection signal. The signal processing circuit processes the detection signal to generate the first processing signal. The control unit calculates the blood oxygen value, the pulse rate, and the signal strength index according to the first processing signal. The control unit outputs the blood oxygen value, the pulse rate, and the signal strength index, or performs low perfusion signal measurement process according to the signal strength index and the first predetermined index. Therefore, the accuracy of the blood oxygen concentration measurement may be effectively increased, and the convenience of use is increased. In the embodiment, when the low perfusion signal measurement process is performed, the current-to-voltage gain, the linear gain and the filter bandwidth in the parameter setting may be adjusted further, so as to effectively improve the signal-to-noise ratio of the signal, obtain more signal information, increase the accuracy of blood oxygen concentration measurement, and increase the convenience of use.

While the present invention has been described by way of example and in terms of the preferred embodiments, it should be understood that the present invention is not limited to the disclosed embodiments. On the contrary, it is intended to cover various modifications and similar arrangements (as would be apparent to those skilled in the art). Therefore, the scope of the appended claims should be accorded the broadest interpretation to encompass all such modifications and similar arrangements.

What is claimed is:

1. A blood oxygen concentration measurement device, comprising:

a light source unit, configured to generate a light signal;

a light detection unit, configured to receive a penetrating signal generated by the light signal penetrating an object to generate a detection signal;

a signal processing circuit, configured to receive the detection signal and process the detection signal to generate a first processing signal; and a control unit, configured to receive the first processing signal, calculate a blood oxygen value, a pulse rate and a signal strength index according to the first processing signal, and output the blood oxygen value, the pulse rate, and the signal strength index or perform a low perfusion signal measurement process according to the signal strength index and a first predetermined index;

wherein the control unit determines whether the signal strength index is greater than the first predetermined index, when the control unit determines that the signal strength index is greater than the first predetermined index, the control unit outputs the blood oxygen value, the pulse rate, and the signal strength index, and when the control unit determines that the signal strength index is not greater than the first predetermined index, the control unit performs the low perfusion signal measurement process;

wherein the control unit further determines whether the first processing signal is within a predetermined measurement range, when the control unit determines that the first processing signal is not within the predetermined measurement range, the control unit controls the signal processing circuit to adjust a driving signal to generate an adjustment signal, so that the light source unit generates the light signal according to the adjustment signal, and when the control unit determines that the first processing signal is within the predetermined measurement range, the control unit calculates the blood oxygen value, the pulse rate, and the signal strength index according to the first processing signal.

2. The blood oxygen concentration measurement device as claimed in claim 1, wherein the light signal comprises a red light signal and an infrared light signal.

3. The blood oxygen concentration measurement device as claimed in claim 1, wherein when the control unit performs the low perfusion signal measurement process, the control unit generates a first parameter setting or a second parameter setting to the signal processing circuit according to the signal strength index and a second predetermined index, so that the signal processing circuit processes the detection signal according to the first parameter setting or the second parameter setting, so as to generate the first processing signal, wherein the second predetermined index is less than the first predetermined index.

4. The blood oxygen concentration measurement device as claimed in claim 3, wherein the control unit determines whether the signal strength index is less than the second predetermined index, when the control unit determines that the signal strength index is not less than the second predetermined index, the control unit generates the first parameter setting to the signal processing circuit, and when the control unit determines that the signal strength index is less than the second predetermined index, the control unit generates the second parameter setting to the signal processing circuit.

5. The blood oxygen concentration measurement device as claimed in claim 3, wherein the first parameter setting comprises an adjusted predetermined measurement range, a reduced current-to-voltage gain, a maintained linear gain, and an expanded filter bandwidth, the signal processing circuit converts the detection signal according to the reduced current-to-voltage gain to generate a voltage signal, multiplies the voltage signal by the maintained linear gain to generate a gain signal, and filters the gain signal according to the expanded filter bandwidth to generate the first processing signal.

6. The blood oxygen concentration measurement device as claimed in claim 3, wherein the second parameter setting comprises an adjusted predetermined measurement range, a current signal, an amplified current-to-voltage gain, an amplified linear gain and an expanded filter bandwidth, the signal processing circuit generates the current signal, subtracts the current signal from the detection signal to generate a second processing signal, converts the second processing signal according to the amplified current-to-voltage gain to generate a voltage signal, multiplies the voltage signal by the amplified linear gain to generate a gain signal, and filters the gain signal according to the expanded filter bandwidth to generate the first processing signal.

7. A blood oxygen concentration measurement method, comprising:

using a light source unit to generate a light signal;

using a light detection unit to receive a penetrating signal generated by the light signal penetrating an object to generate a detection signal;

using a signal processing circuit to receive the detection signal and process the detection signal to generate a first processing signal;

using a control unit to receive the first processing signal;

using the control unit to calculate a blood oxygen value, a pulse rate, and a signal strength index according to the first processing signal;

using the control unit to output the blood oxygen value, the pulse rate, and the signal strength index or perform a low perfusion signal measurement process according to the signal strength index and a first predetermined index;

the control unit determining whether the first processing signal is within a predetermined measurement range;

when the control unit determines that the first processing signal is not within the predetermined measurement range, the control unit controlling the signal processing circuit to adjust a driving signal to generate an adjustment signal, and performs the step of using the light source unit to generate the light signal; and when the control unit determines that the first processing signal is within the predetermined measurement range, performing the step of using the control unit to calculate the blood oxygen value, the pulse rate, and the signal strength index according to the first processing signal;

wherein the step of outputting the blood oxygen value, the pulse rate, and the signal strength index, or of performing the low perfusion signal measurement process according to the signal strength index and a first predetermined index, comprises:

determining whether the signal strength index is greater than the first predetermined index;

when the control unit determines that the signal strength index is greater than the first predetermined index, the control unit outputting the blood oxygen value, the pulse rate, and the signal strength index; and when the control unit determines that the signal strength index is not greater than the first predetermined index, the control unit performing the low perfusion signal measurement process.

8. The blood oxygen concentration measurement method as claimed in claim 7, wherein the light signal comprises a red light signal and an infrared light signal.

9. The blood oxygen concentration measurement method as claimed in claim 7, wherein the step of the control unit performing the low perfusion signal measurement process comprises:

the control unit generating a first parameter setting or a second parameter setting to the signal processing circuit according to the signal strength index and a second predetermined index;

wherein the step of the signal processing circuit processing the detection signal to generate the first processing signal comprises:

the signal processing circuit processing the detection signal according to the first parameter setting or the second parameter setting, so as to generate the first processing signal;

wherein the second predetermined index is less than the first predetermined index.

10. The blood oxygen concentration measurement method as claimed in claim 9, wherein the step of the control unit generating the first parameter setting or the second parameter setting to the signal processing circuit according to the signal strength index and the second predetermined index comprises:

the control unit determining whether the signal strength index is less than the second predetermined index;

when the control unit determines that the signal strength index is not less than the second predetermined index, generating the first parameter setting to the signal processing circuit; and when the control unit determines that the signal strength index is less than the second predetermined index, generating the second parameter setting to the signal processing circuit.

11. The blood oxygen concentration measurement method as claimed in claim 9, wherein the first parameter setting comprises an adjusted predetermined measurement range, a reduced current-to-voltage gain, a maintained linear gain, and an expanded filter bandwidth, and the step of the signal processing circuit processing the detection signal according to the first parameter setting, so as to generate the first processing signal comprises:

the signal processing circuit converting the detection signal according to the reduced current-to-voltage gain to generate a voltage signal;

multiplying the voltage signal by the maintained linear gain to generate a gain signal; and filtering the gain signal according to the expanded filter bandwidth to generate the first processing signal.

12. The blood oxygen concentration measurement method as claimed in claim 9, wherein the second parameter setting comprises an adjusted predetermined measurement range, a current signal, an amplified current-to-voltage gain, an amplified linear gain and an expanded filter bandwidth, and the step of the signal processing circuit processing the detection signal according to the second parameter setting, so as to generate the first processing signal comprises:

the signal processing circuit generating the current signal;

subtracting the current signal from the detection signal to generate a second processing signal;

converting the second processing signal according to the amplified current-to-voltage gain to generate a voltage signal;

multiplying the voltage signal by the amplified linear gain to generate a gain signal; and filtering the gain signal according to the expanded filter bandwidth to generate the first processing signal.

* * * * *